US010383761B2

(12) United States Patent
Fallon

(10) Patent No.: US 10,383,761 B2
(45) Date of Patent: Aug. 20, 2019

(54) JAW ADVANCEMENT ORAL APPLIANCE TO REDUCE THE EFFECTS OF SNORING AND/OR SLEEP APNEA

(71) Applicant: James S Fallon, Laguna Niguel, CA (US)

(72) Inventor: James S Fallon, Laguna Niguel, CA (US)

( * ) Notice: Subject to any disclaimer, the term of this patent is extended or adjusted under 35 U.S.C. 154(b) by 597 days.

(21) Appl. No.: 15/229,715

(22) Filed: Aug. 5, 2016

(65) Prior Publication Data

US 2018/0036165 A1 Feb. 8, 2018

(51) Int. Cl.
*A61F 5/56* (2006.01)

(52) U.S. Cl.
CPC .................. *A61F 5/566* (2013.01)

(58) Field of Classification Search
CPC ...... A61F 5/566; A61F 5/56; A61F 2005/563; A61F 5/58; A61F 5/0102; A61F 2005/0137; A61F 2005/0139; A61F 2005/0153; A61F 5/026; A61F 5/028; A61F 2210/009; A61F 2250/0067; A61F 2/0022; A61F 2/28; A61F 2/30; A61F 2/36; A61F 2/94; A61F 5/0125; A61F 5/055; A61F 2002/9528; A61F 2250/0004; A61F 2250/0065; A61F 2/013; A61F 2/14; A61F 2/82; A61F 2/95; A61F 5/013; A61F 9/007; A61F 9/00727; A61C 7/08; A61C 19/063; A61B 5/4547; A61B 5/4552; A61B 5/4557; A61B 5/682; A61B 5/0534; A63B 71/085; A63B 2071/086; A63B 2017/088; Y10S 602/902; A61N 2/00; A61N 2/002; A61N 2/004; A61N 2/006; A61N 2/008; A61N 1/40; G09B 19/003; G09B 23/28; Y10T 29/49826

See application file for complete search history.

(56) References Cited

U.S. PATENT DOCUMENTS

| 8,833,374 B2 | 9/2014 | Fallon | |
| 2009/0272387 A1* | 11/2009 | Spencer | A61F 5/566 128/848 |
| 2012/0148978 A1* | 6/2012 | Suchan | A61C 9/0006 433/38 |
| 2015/0164682 A1* | 6/2015 | Remmers | A61B 5/4812 600/301 |
| 2017/0258560 A1* | 9/2017 | Llop | A61C 9/0006 |

* cited by examiner

*Primary Examiner* — Tarla R Patel
(74) *Attorney, Agent, or Firm* — Morland C. Fischer

(57) ABSTRACT

A jaw advancement oral appliance is disclosed to be inserted in the mouth of a user to maintain an airway to the user's throat during sleep. The appliance includes an upper tray assembly against which the user's teeth carried by his upper jaw are seated and a lower tray assembly against which the user's teeth carried by his lower jaw are seated. Each tray assembly includes a bite impression tray having a plurality of holes formed therein and arranged in a honeycomb pattern. The bite impression trays are manufactured from a soft material so that a custom impression of the user's teeth is created when the appliance is heated and the user bites into the bite impression trays.

10 Claims, 6 Drawing Sheets

US 10,383,761 B2

JAW ADVANCEMENT ORAL APPLIANCE TO REDUCE THE EFFECTS OF SNORING AND/OR SLEEP APNEA

BACKGROUND OF THE INVENTION

1. Field of the Invention

This invention relates to a jaw advancement oral appliance to be worn in the mouth and over the teeth of a user during sleep to reduce the effects of snoring and/or sleep apnea. The jaw advancement oral appliance includes upper and lower tray assemblies having an open cell honeycomb configuration to be initially heated and softened so as to create a custom impression of the user's teeth when the user bites into the appliance when it is prepared for its first use.

2. Background Art

U.S. Pat. No. 8,833,374 issued Sep. 16, 2014 and entitled INTRA-ORAL MANDIBULAR ADVANCEMENT APPLIANCE describes a unique oral appliance to be inserted in the mouth and worn over the teeth of a user to maintain an open airway through the appliance and to the user's throat to thereby improve the user's breathing during sleep. The patented appliance has particular application for use by those wishing to reduce the effects of snoring and/or sleep apnea. The appliance includes upper and lower tray assemblies against which the user's upper and lower sets of teeth are seated during use. The lower tray assembly is slidably adjustable relative to the upper tray assembly to correspondingly and selectively adjust the position of the user's lower jaw relative to his upper jaw in order to keep the aforementioned airway open as the user's condition changes over time.

Depending upon how the user sleeps and moves about, the position of the patented oral appliance could shift in the user's mouth relative to his upper and lower sets of teeth. In some cases, the appliance might fall completely out of the user's mouth and thereby be rendered ineffective. What would therefore be desirable is an improved jaw advancement oral appliance similar to that described above, but having a unique structural configuration by which to enable the appliance to remain in place over and around the user's teeth throughout the night so that the airway to the user's throat will remain open.

SUMMARY OF THE INVENTION

In general terms, a jaw advancement oral appliance is disclosed to be worn in the mouth and over the teeth of a user during sleep to reduce the effects of snoring and/or sleep apnea. The oral appliance includes flexible upper and lower arcuate shaped tray assemblies which are engaged by the user's upper and lower sets of teeth during sleep. Each of the upper and lower tray assemblies includes a relatively soft (e.g., copolymer) and impressionable bite impression tray against which the user's teeth are pressed and a relative hard (e.g., polycarbonate) chassis over which a bite impression tray is molded. A pair of position adjustment blocks extend upwardly from opposite ends of the chassis of the lower tray assembly for slidable receipt within respective locking channels formed in opposite ends of the opposing chassis of the upper tray assembly. Each of the position adjustment blocks and the locking channels has a set of teeth which run along one side thereof to be moved into mating engagement with one another so as to hold the position adjustment blocks within the locking channels and thereby lock the lower tray assembly in place relative to the upper tray assembly.

When it is desirable to displace the lower tray assembly of the jaw advancement oral appliance relative to the upper tray assembly so that the user's lower jaw will be repositioned relative to his upper jaw during sleep, squeezing forces are momentarily applied in opposite directions to the opposite sides of the flexible upper tray assembly. As a result of the squeezing forces, the upper tray assembly is temporarily compressed such that the teeth at one side of the locking channels thereof are moved out of their former mating engagement with the teeth at one side of the position adjustment blocks. A pushing force is now applied to the lower tray assembly to cause the position adjustment blocks to slide through the locking channels and the lower tray assembly to correspondingly move relative to the upper tray assembly. Once the position of the lower tray assembly and the user's lower jaw has been adjusted, the momentary squeezing forces are terminated. Accordingly, the upper tray assembly will now expand back to its original shape, whereby the teeth of the locking channels move back into mating engagement with the teeth of the position control blocks to once again lock the lower tray assembly in place at its new position relative to the upper tray assembly.

As an important feature of the jaw advancement oral appliance of this invention, each of the bite impression trays of the upper and lower tray assemblies against which the user's teeth are pressed during sleep is provided with a set of open cells or holes extending therearound. Each of the sets of holes formed in the bite impression trays of the upper and lower tray assemblies is preferably arranged in a honeycomb pattern, and each hole preferably has a hexagonal shape. Prior to its first use, the oral appliance is heated in boiling water to soften the bite impression trays. As the user bites against the softened bite impression trays in which the honeycomb patterns of holes are formed, the relatively soft and impressionable (e.g., copolymer) material of the bite impression trays will uniformly flow up, over and around the user's teeth to create a custom impression thereof. By virtue of this custom impression, the oral appliance will fit snugly around and adhere to the user's teeth so as to be unlikely to shift or fall out of the user's mouth when the appliance is worn over the user's teeth during sleep.

DESCRIPTION OF THE PREFERRED EMBODIMENT

Figure 1:
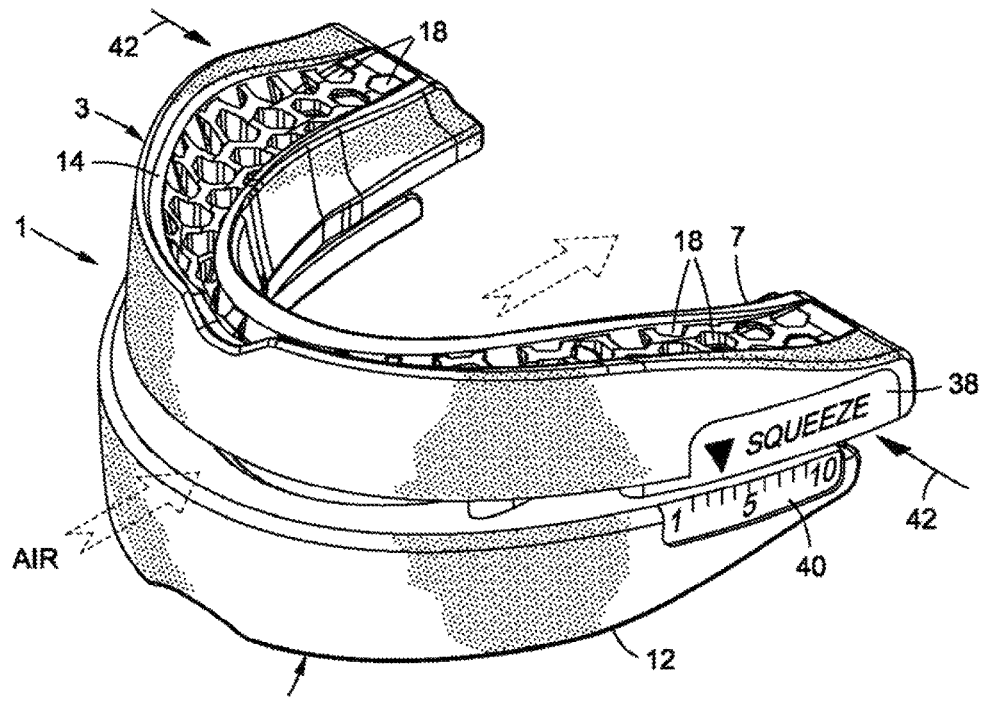
FIG. 1 is a top perspective view showing a jaw advancement oral appliance according to a preferred embodiment of this invention.
Figure 2:
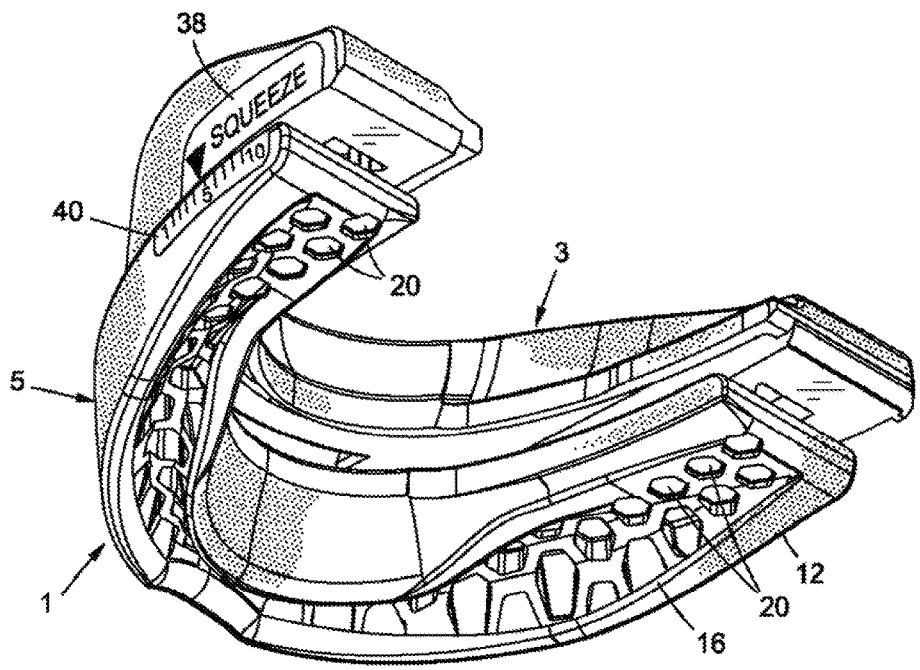
FIG. 2 is a bottom perspective view of the jaw advancement oral appliance shown in FIG. 1.

Turning to the drawings, details are provided of a jaw advancement oral appliance 1 that is sized to fit within the mouth and over the teeth of a user so that the user's lower jaw can be repositioned relative to his upper jaw by a variable distance that can be selectively and continuously controlled by the user. By virtue of the foregoing, the oral appliance 1 can be manually adjusted by the user without the use of tools, springs, the removal and insertion of fasteners, or the intervention by medical personnel so that a continuous air path (illustrated in FIG. 1) through the oral appliance to the user's throat will remain open while the user sleeps. It may therefore be appreciated that the oral appliance 1 has particular application for use during sleep by one wishing to cope with the effects of snoring and/or sleep apnea.

Referring initially to FIGS. 1-8 of the drawings, the jaw advancement oral appliance 1 includes a flexible upper tray assembly 3 and a flexible lower tray assembly 5 that are spaced one above the other so as to create the aforementioned air path therebetween. As will be described in greater detail hereinafter, the upper and lower tray assemblies 3 and 5 are coupled to one another such that the lower tray assembly 5 can be moved by the user relative to upper tray assembly 3. For example, a forward displacement of the lower tray assembly 5 illustrated in FIG. 3 results in a forward displacement of the user's lower jaw relative to his upper jaw to enable the size of the air path to the user's throat to be regulated in order to reduce the effects of snoring and/or sleep apnea.

Figure 8:
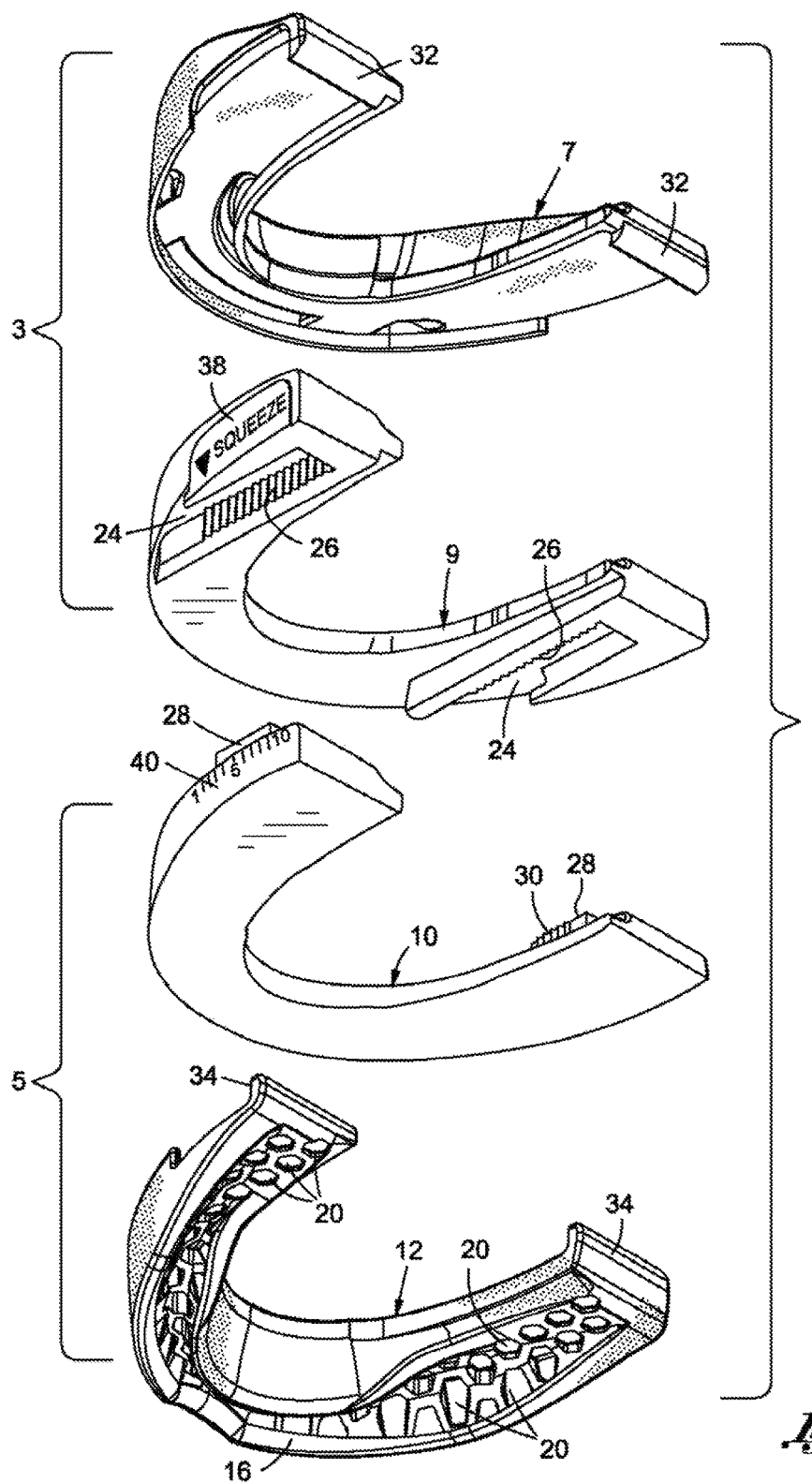
FIG. 8 is an exploded view of the jaw advancement oral appliance shown in FIG. 2.

As is best shown in FIG. 8, the upper tray assembly 3 of the jaw advancement oral appliance 1 includes an upper bite impression tray 7 and an upper chassis 9 that are molded together so that the upper bite impression tray 7 lies above the upper chassis 9. Both the upper bite impression tray 7 and upper chassis 9 have a generally arcuate configuration to match the bite pattern of the teeth carried by the user's upper jaw. The upper bite impression tray 7 is manufactured from a relatively soft and impressionable copolymer material such as, for example, ethylene vinyl acetate or that known commercially as EVA manufactured by DuPont. The upper chassis 9 is manufactured from a relatively hard and rigid material such as, for example, polycarbonate or a plastic known commercially as MAKROLOR® 2558.

The lower tray assembly 5 of the jaw advancement oral appliance 1 includes a lower chassis 10 and a lower bite impression tray 12 that are molded together so that the lower chassis 10 lies above the lower bite impression tray 12. Like the upper bite impression tray 7 and the upper chassis 9 of the upper tray assembly 3, the lower chassis 10 and the lower bite impression tray 12 of the lower tray assembly 5 each have a generally arcuate configuration to match the bite pattern of the teeth carried by the user's lower jaw. The lower chassis 10 of the lower tray assembly 5 is preferably manufactured from the same relatively soft and impressionable material as the upper chassis 9 of the upper tray assembly 3, and the lower bite impression tray 12 of the lower tray assembly 5 is preferably manufactured from the same soft material as the upper bite impression tray 7 of the upper tray assembly 3.

An upper bite channel 14 (best shown in FIGS. 1, 4 and 5) runs around the top of the arcuate upper bite impression tray 7 of the upper tray assembly 3. The bite channel 14 is sized to receive therewithin the set of teeth of the user carried by his upper jaw. Inasmuch as the relatively soft upper bite impression tray 7 lays over and against the relatively hard upper chassis 9, a biting force generated by the user's upper set of teeth and applied to the upper bite impression tray 7 can initially shape the bite channel 14 thereof in a manner that will soon be described.

A lower bite channel 16 (best shown in FIGS. 2, 6 and 7) runs around the bottom of the arcuate lower bite impression tray 12 of the lower tray assembly 5. The lower bite channel 16 is sized to receive therewithin the set of teeth of the user carried by his lower jaw. Inasmuch as the relatively soft lower bite impression tray 12 lays below and against the relatively hard lower chassis 10, a biting force generated by the user's lower set of teeth and applied to the lower bite impression tray 12 can initially shape the lower bite channel 16 at the same time that the upper bite channel 14 from the upper bite impression tray 7 is being shaped.

As an important feature of the oral appliance 1, both the upper bite channel 14 of the upper bite impression tray 7 and the lower bite channel 16 of the lower bite impression tray 12 are provided with respective sets 18 and 20 of open cells or holes formed therein. By way of a preferred example only, the sets 18 and 20 of holes are arranged in a honeycomb pattern, and each hole has a hexagonal shape. The holes from each of the sets 18 and 20 of holes are uniformly spaced from one another and extend continually around the upper and lower bite channels 14 and 16. The sets of holes 18 and 20 are ideally molded into the relatively soft upper and lower bite channels 14 and 16 during the manufacture of the upper and lower bite impression trays 7 and 12. It is to be understood, however, that the particular shape and number of holes from the first and second sets 18 and 20 of holes are not to be considered as a limitation to this invention.

The aforementioned sets 18 and 20 of holes that are formed around the upper and lower bite channels 14 and 16 of the upper and lower bite impression trays 7 and 12 advantageously enable a custom fit of the jaw advancement oral appliance 1 in surrounding engagement with the user's upper and lower sets of teeth when the oral appliance is initially prepared for use. That is, and as will be explained in greater detail when referring to FIG. 9, the upper and lower tray assemblies 3 and 5 of the appliance 1 are first heated and then placed into the user's mouth. Next the user bites on the upper and lower impression trays 7 and 12 so that an impression of his teeth will be made therein.

Because the upper and lower bite impression trays 7 and 12 are manufactured from a relatively soft impressionable (e.g., copolymer) material, the sets 18 and 20 of holes formed in the upper and lower bite channels 14 and 16 enable the heated material to uniformly flow up, over and around the user's teeth in response to the compression force generated when the user bites on the upper and lower bite impression trays 7 and 12. Accordingly, the impression made in the upper and lower bite channels 14 and 16 will closely conform to the shape of the user's teeth so that the oral appliance 1 will fit snugly around and adhere to the user's teeth so as to be unlikely to shift or fall out of the user's mouth during sleep.

Referring specifically to FIG. 8, a recessed locking channel 24 is shown formed (e.g., molded) into the bottom and at each side of the arcuate upper chassis 9 of the upper tray assembly 3 of the oral appliance 1. The locking channels 24 run parallel to one another. A row of teeth 26 is formed (e.g., molded) along one side of each locking channel 24. Located at opposite sides of and standing upwardly from the arcuate lower chassis 10 of the lower tray assembly 5 of oral appliance 1 are a pair of position adjustment blocks 28. A row of teeth 30 (only one of which being visible) is formed (e.g., molded) along one side of each position control block 28.

During the assembly of the jaw advancement oral appliance 1, the upper tray assembly 3 is completed when the upper bite impression tray 7 is molded over and against the top of the upper chassis 9. A locking tail 32 which extends outwardly from each end of the upper bite impression tray 7 bends around and engages an opposing end of the upper chassis 9 to hold the upper bite impression tray 7 over the top of the upper chassis 9. The lower tray assembly 5 is completed when the lower bite impression tray 12 is molded over and against the bottom of the lower chassis 10. A locking tail 34 which extends outwardly from each end of the lower bite impression tray 12 bends around and engages an opposing end of the lower chassis 10.

Next, the upper tray assembly 3 is slidably mounted on top of the lower tray assembly 5. To accomplish the foregoing, the pair of position adjustment blocks 28 which stand upwardly from the lower chassis 10 of the lower tray assembly 5 are pushing into slidable receipt by respective ones of the pair of locking channels 24 formed in the upper chassis 9 of the upper tray assembly 3, whereby the upper and lower tray assemblies 3 and 5 are coupled together and held one over the other. In this same regard, the rows of teeth 30 which run along the pair of upstanding position adjustment blocks 28 are moved into releasable locking engagement with and mesh against the rows of teeth 26 which run along the pair of locking channels 24. However, it may be appreciated that any suitable interlocking ratchet means may be substituted for the opposing rows of teeth 26 and 30.

By virtue of the foregoing, the user is provided with the ability to release the locking meshing engagement of the teeth 30 of the position adjustment blocks 28 with the teeth 26 of the locking channels 24. Accordingly, as illustrated in FIG. 3, the position of the lower tray assembly 5 of the jaw advancement oral appliance 1 can be selectively changed relative to the upper tray assembly 3 to meet the changing needs of the patient over time.

A pair of position control pads 38 are located at and molded into opposite sides of the upper chassis 9 of the upper tray assembly 3. A position indication scale 40 is molded into or printed onto each side of the lower chassis 10 of the lower tray assembly 5 so as to lie below a position control pad 38. The upper tray assembly 3 is responsive to momentary compressive squeezing forces (represented by the directional arrows 42 in FIG. 1) simultaneously applied in opposite directions at the position control pads 38 thereof to temporarily compress and change the shape of the upper tray assembly 3 whereby the opposite sides of the upper tray assembly 3 are squeezed towards one another. At the same time, the teeth 26 of the locking channels 24 of the upper chassis 9 are temporarily moved out of their locking engagement with the teeth 30 of the position adjustment blocks 28 of the lower chassis 10 of the lower tray assembly 5. Although in a preferred embodiment, the compressive squeezing forces 42 are applied to the upper tray assembly 3, it is within the scope of this invention to apply the squeezing forces instead to the lower tray assembly 5 to temporarily compress and change the shape thereof.

Figure 3:
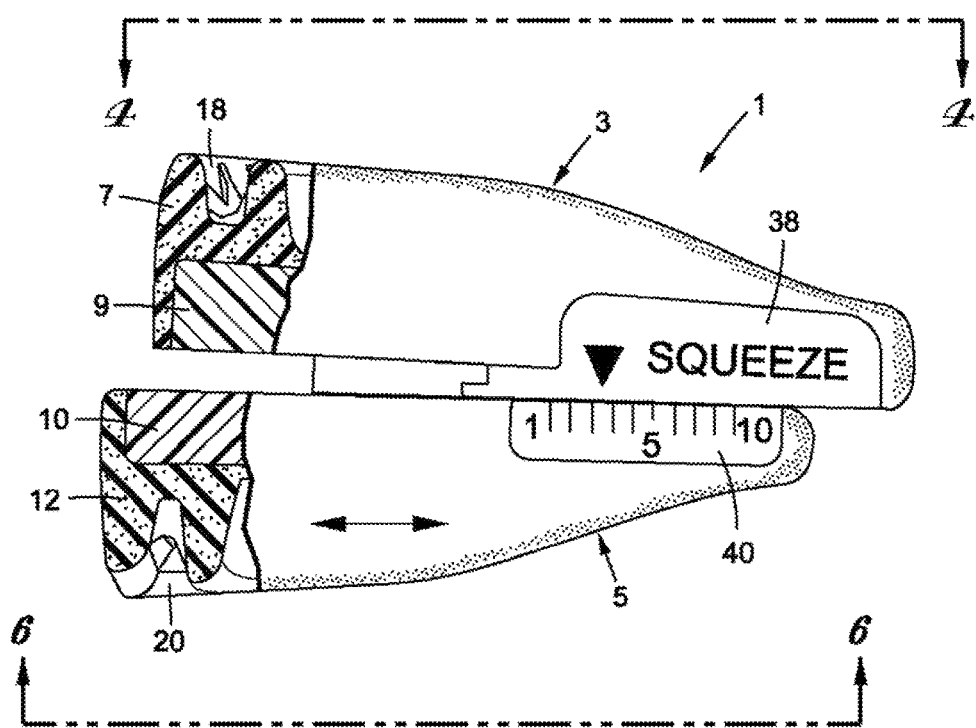
FIG. 3 illustrates the position of a lower tray assembly of the jaw advancement oral appliance being adjusted relative to an upper tray assembly thereof.
Figure 5:
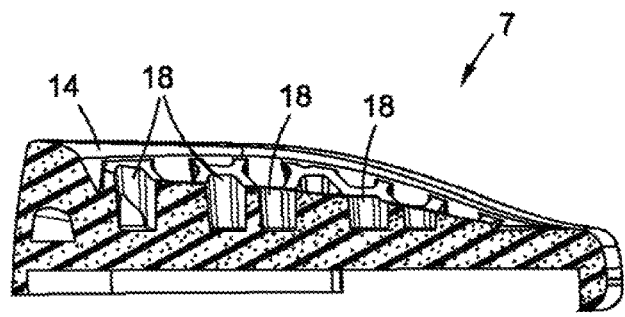
FIG. 5 is a cross section of the jaw advancement oral appliance taken along lines 5-5 of FIG. 4.
Figure 4:
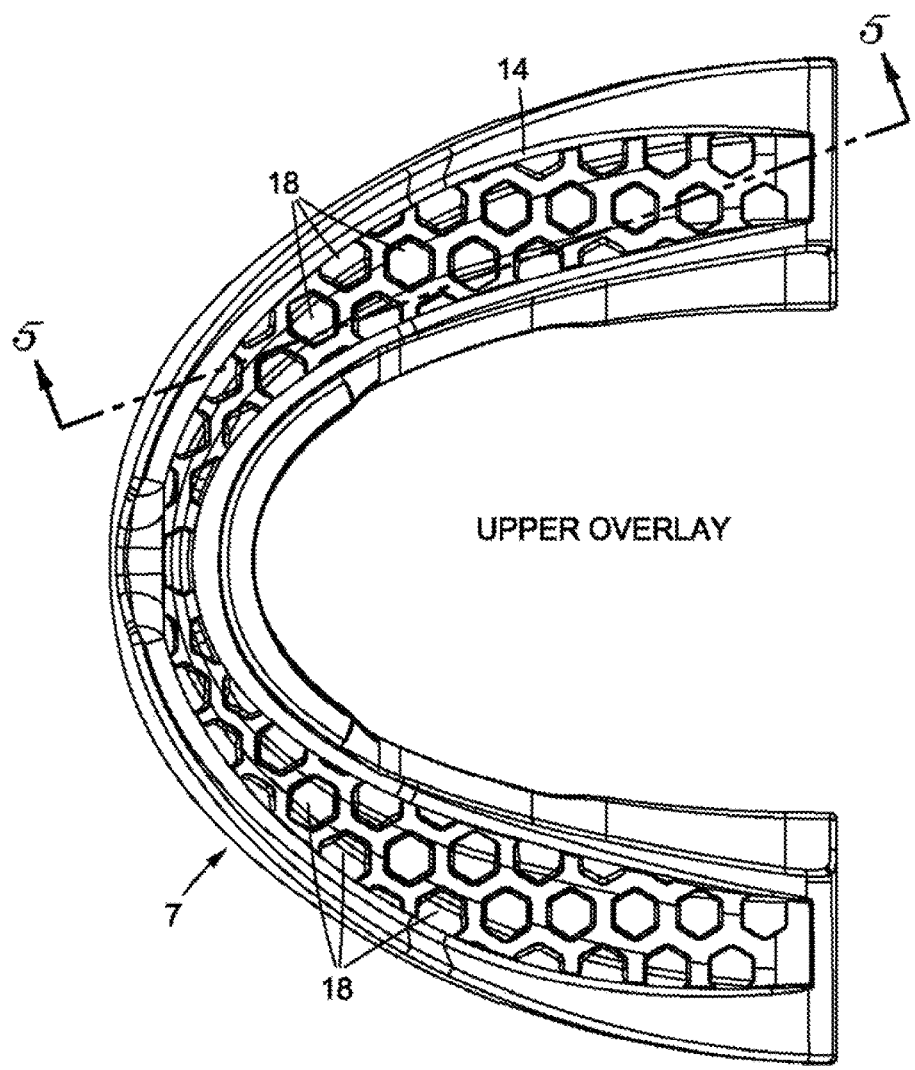
FIG. 4 is a top view of the jaw advancement oral appliance taken in the direction of lines 4-4 of FIG. 3.
Figure 7:
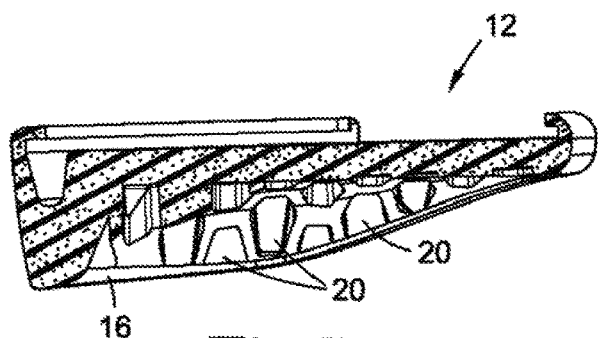
FIG. 7 is a cross section of the jaw advancement oral appliance taken along lines 7-7 of FIG. 6.
Figure 6:
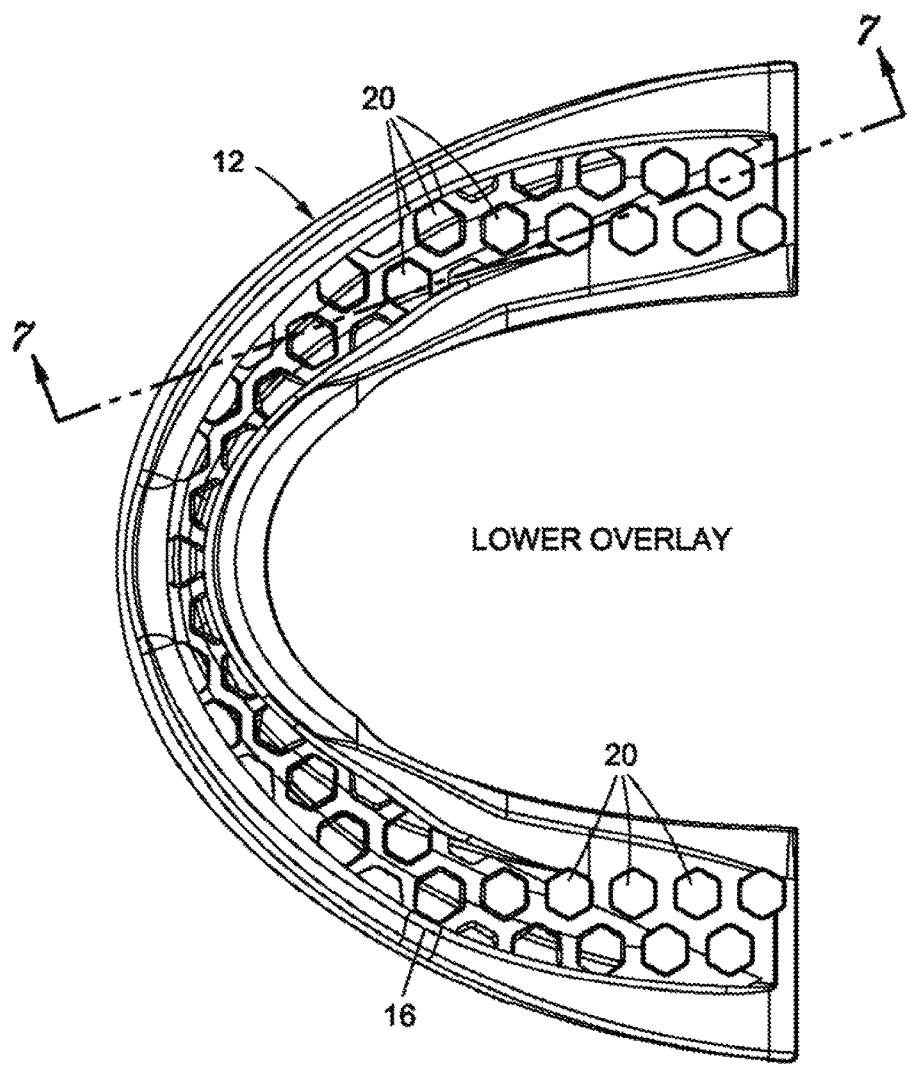
FIG. 6 is a bottom view of the jaw advancement oral appliance taken in the direction of lines 6-6 of FIG. 3.

As is best shown in FIG. 3, the user can now apply a pushing (or pulling) force to relocate and change the position of the lower tray assembly 5 relative to the upper tray assembly 3. In the alternative, the user can also apply a pushing or pulling force to the upper tray assembly 3 to relocate and change the position of the upper tray assembly 3 relative to the lower tray assembly 5. In either case, the pair of position adjustment blocks 28 will slide through respective ones of the pair of locking channels 24.

When the position of one of the upper or lower tray assemblies 3 or 5 has been adjusted relative to the other one, the compressive squeezing forces are terminated. Accordingly, the formerly compressed upper tray assembly 3 will automatically expand back to its initial shape. At the same time, the teeth 26 of the locking channels 24 will move back into mating interlocking engagement with the opposing teeth of the position adjustment blocks 28 so that the upper and lower tray assemblies 3 and 5 will once again be held in place one above the other. The location of the position control pads 38 above the position indication scales 40 provides the user with a visual indication of the position of the lower tray assembly 5 with respect to the upper tray assembly 3 so that the user can make regular controllable and precise position adjustments of the lower tray assembly 5 to correspondingly change the position of his lower jaw relative to his upper jaw.

Figure 9:
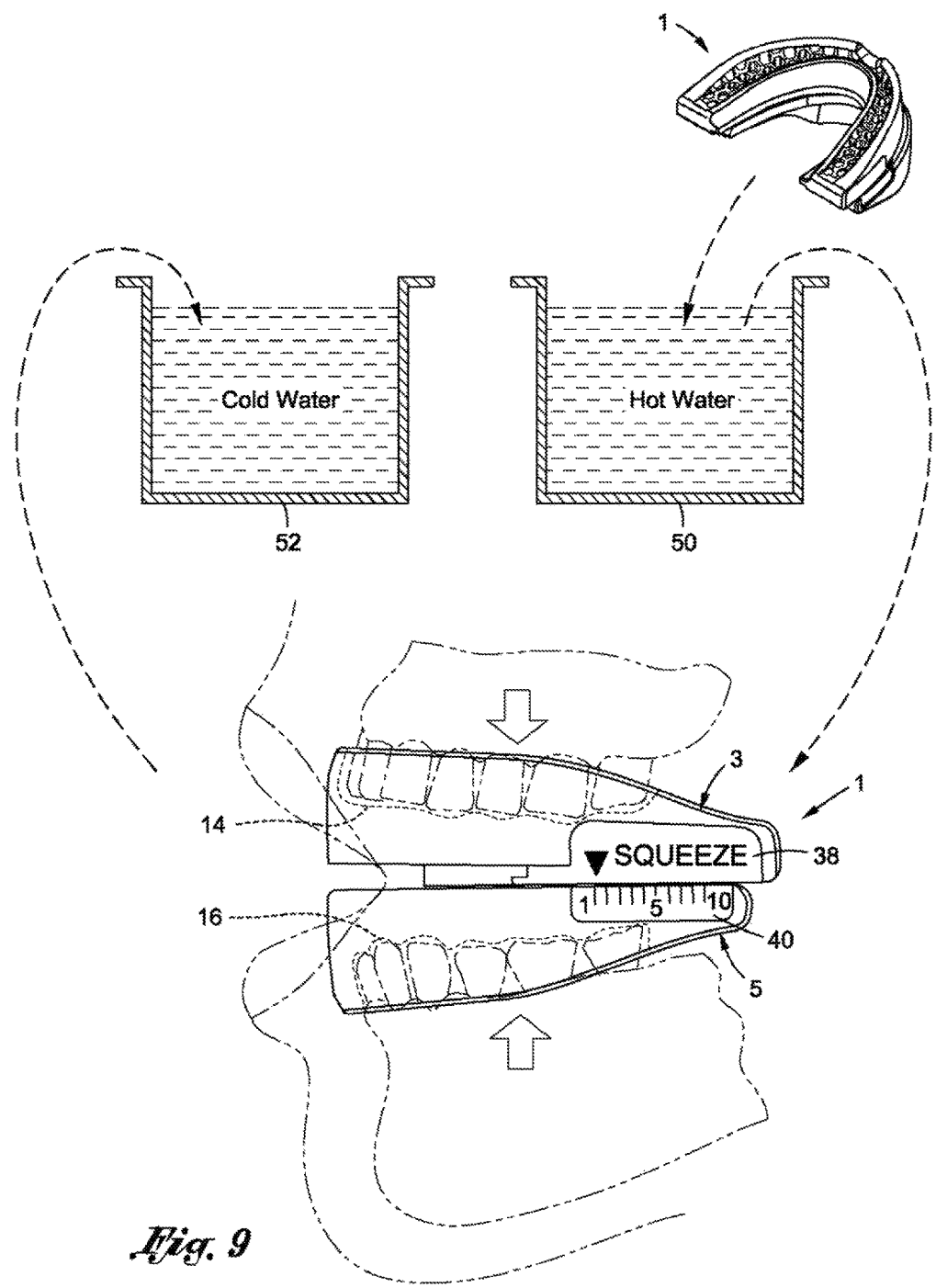
FIG. 9 illustrates the steps of first heating and then biting into sets of open cell holes formed in the upper and lower tray assemblies of the jaw advancement oral appliance to create a custom impression of a user's teeth prior to the initial use of the oral appliance during sleep.

Turning now to FIG. 9 of the drawings, the advantage is explained of the upper and lower sets 18 and 20 of open cells or holes that are formed in and around the upper and lower bite channels 14 and 16 of the upper and lower tray assemblies 3 and 5 of the jaw advancement appliance 1 shown in FIGS. 1-6. More particularly, prior to using the oral appliance 1 for the first time during sleep, the user boils a pot of water 50 within which the oral appliance is placed and heated. The heated oral appliance 1 is then removed from the boiling water by means of tongs or a similar tool and permitted to cool until it becomes warm.

While still warm, the oral appliance 1 is inserted in the user's mouth at which time the user closes his mouth and bites on the relatively soft upper bite impression tray 7 and the lower bite impression tray 12. The user's upper set of teeth bite down against the upper bite channel 14 of the upper bite impression tray 7, and his lower set of teeth bite up against the lower bite channel 16 of the lower bite impression tray 12. By virtue of the honeycomb patterns of the sets of holes 18 and 20 and the relatively soft (e.g., copolymer) material of the upper and lower bite impression trays 7 and 12, at least some of the holes from each set thereof will communicate with one another, whereby the impressionable material at the bite impression trays 7 and 12 will be uniformly displaced and flow evenly around the edges and the crevices of the user's teeth. Therefore, accurate impressions of the user's upper and lower sets of teeth are shaped in the opposing bite channels 7 and 12 which lay on and are compressed against the relatively hard upper and lower chassis 9 and 10 of the upper and lower tray assemblies 3 and 5.

After biting on the oral appliance 1 for about 30 seconds, the appliance is removed from the user's mouth and placed into a pot of cold water 52 where it is cooled. The jaw advancement oral appliance of this invention is now ready to be used during sleep at which time the oral appliance is again inserted in the mouth of the user. As previously explained the appliance 1 is advantageously adapted to position and controllably reposition the patient's lower jaw forward of his upper jaw so that an airway will be kept open to the user's throat so as to minimize the effects of snoring and/or sleep apnea.

The invention claimed is:

1. A jaw advancement oral appliance to be inserted in the mouth of a user in order to adjust the position of the user's lower jaw relative to his upper jaw to maintain an airway to the throat through which the user can breathe while sleeping, said oral appliance comprising:

an upper tray assembly having a heat responsive upper bite impression tray against which the upper teeth of the user's upper jaw are seated during sleep, said heat responsive upper bite impression tray having a plurality of holes formed therein so as to be softened when heated and flow up and around the upper teeth of the user's upper jaw by which an impression of the user's upper teeth is made when the user bites down on said upper bite impression tray; and a lower tray assembly having a heat responsive lower bite impression tray against which the lower teeth of the user's lower jaw are seated during sleep, said heat responsive lower bite impression tray having a plurality of holes formed therein so as to be softened when heated and flow down and around the lower teeth of the user's lower jaw by which an impression of the user's lower teeth is made when the user bites up on said lower bite impression tray;

said upper and lower tray assemblies being coupled together in releasable locking engagement one above the other to prevent a displacement of said lower tray assembly relative to said upper tray assembly, and one of said upper tray assembly or said lower tray assembly being responsive to a compressive force momentarily applied thereto by which the shape thereof is temporarily changed so as to release the locking engagement between said upper and lower tray assemblies to thereby enable the position of said lower tray assembly to be adjusted relative to the position of said upper tray assembly.

2. The jaw advancement oral appliance recited in claim 1, wherein said plurality of holes extend continually along respective ones of said heat responsive upper and lower bite impression trays of said upper and lower tray assemblies.

3. The jaw advancement oral appliance recited in claim 2, wherein said pluralities of holes are formed in respective ones of said heat responsive upper and lower bite impression trays of said upper and lower tray assemblies, such that at least some of said holes communicate with one another when said upper and lower bite impression trays are heated and softened and the user bites into said upper and lower bite impression trays.

4. The jaw advancement oral appliance recited in claim 2, wherein at least some of the holes of the plurality of holes formed in each of said heat responsive upper and lower bite impression trays has a hexagonal shape.

5. The jaw advancement oral appliance recited in claim 4, wherein the holes of the plurality of holes formed in each of said heat responsive upper and lower bite impression trays are uniformly spaced from one another and arranged in a honeycomb pattern.

6. The jaw advancement oral appliance recited in claim 1, wherein said upper tray assembly also has an upper chassis above which said heat responsive upper bite impression tray is located, said upper bite impression tray being manufactured from a material that is softer and more impressionable in response to heat than the material from which said upper chassis is manufactured; and wherein said lower tray assembly also has a lower chassis below which said heat responsive lower bite impression tray is located, said lower bite impression tray manufactured from a material that is softer and more impressionable in response to heat than the material from which said lower chassis is manufactured.

7. The jaw advancement oral appliance recited in claim 1, wherein each of said upper and lower tray assemblies has an arcuate shape with a front and a pair of sides that are spaced from one another, said arcuate lower tray assembly having a position adjustment block located at each one of said pair of sides thereof and said arcuate upper tray assembly having a locking channel located at each one of said pair of sides thereof, each position adjustment block being received within and slidable through a respective locking channel when the position of said lower tray assembly is adjusted relative to the position of said upper tray assembly.

8. The jaw advancement oral appliance recited in claim 7, wherein each of the position adjustment blocks and each of the locking channels located at the pair of sides of each of said arcuate upper and lower tray assemblies has a set of teeth running therealong, the sets of teeth of the position adjustment blocks meshing with the sets of teeth of said locking channels, whereby said lower tray assembly is mated in said releasable locking engagement to said upper tray assembly to prevent a displacement of said lower tray assembly relative to said upper tray assembly.

9. The jaw advancement oral appliance recited in claim 7, wherein the one of said arcuate upper tray assembly or said arcuate lower tray assembly to which said compressive force is momentarily applied is flexible, said compressive force being simultaneously applied in opposite directions to respective ones of the pair of sides of said one tray assembly to cause a corresponding temporary compression of said one tray assembly such that the pair of sides thereby move towards one another.

10. The jaw advancement oral appliance recited in claim 9, wherein the one of said arcuate upper tray assembly or said arcuate lower tray assembly that is temporary compressed when said compressive force is momentarily applied thereto automatically expands such that the pair of sides thereof move away from one another when the compressive force is terminated.

* * * * *